(12) United States Patent
Takeuchi et al.

(10) Patent No.: US 9,476,834 B2
(45) Date of Patent: Oct. 25, 2016

(54) PROCESS FOR PRODUCING SUPRAMOLECULAR FIBER

(75) Inventors: Shoji Takeuchi, Tokyo (JP); Hiroaki Onoe, Tokyo (JP); Daisuke Kiriya, Berkeley, CA (US); Itaru Hamachi, Kyoto (JP); Masato Ikeda, Gifu (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 182 days.

(21) Appl. No.: 13/522,155

(22) PCT Filed: Sep. 17, 2010

(86) PCT No.: PCT/JP2010/066131
§ 371 (c)(1),
(2), (4) Date: Dec. 10, 2012

(87) PCT Pub. No.: WO2011/089753
PCT Pub. Date: Jul. 28, 2011

(65) Prior Publication Data
US 2013/0071948 A1    Mar. 21, 2013

(30) Foreign Application Priority Data

Jan. 20, 2010   (JP) .................................. 2010-009728

(51) Int. Cl.
| | | |
|---|---|---|
| *D01D 5/00* | (2006.01) | |
| *D01D 5/34* | (2006.01) | |
| *D01F 8/18* | (2006.01) | |

(Continued)

(52) U.S. Cl.
CPC ................ *G01N 21/76* (2013.01); *D01D 5/00* (2013.01); *D01D 5/34* (2013.01); *D01F 6/94* (2013.01); *D01F 8/18* (2013.01)

(58) Field of Classification Search
CPC .......... G01N 21/76; D01D 5/00; D01D 5/30; D01D 5/32; D01D 5/34; D01D 5/36; C08G 83/008
USPC ......... 428/378, 373–374; 442/199–202, 311, 442/361–365
See application file for complete search history.

(56) References Cited

U.S. PATENT DOCUMENTS 6,902,932 B2 *  6/2005  Altman et al. ................ 435/395
2010/0076377 A1 *  3/2010  Ehrenreich et al. ..... 604/103.08

(Continued)

FOREIGN PATENT DOCUMENTS

| JP | 2008-221370 | 9/2008 |
| WO | WO 2008150970 A2 * | 12/2008 |
| WO | 2009/005152 | 1/2009 |

OTHER PUBLICATIONS

Virginia Tech, Reversible Process for Forming Supramolecular Polymers Could Be the Basis of Fibers, Molecular Transport Mechanisms. Mar. 23, 1999. ScienceDaily. Retrieved Jun. 6, 2013, from http://www.sciencedaily.com/releases/1999/03/990323045900.htm.*

(Continued)

*Primary Examiner* — Jennifer Chriss
*Assistant Examiner* — Frank Vineis
(74) *Attorney, Agent, or Firm* — Greenblum & Bernstein, P.L.C.

(57) ABSTRACT

A method for preparing a linearly extended supramolecular fiber or a plurality of linearly aligned supramolecular fibers, which comprises the step of allowing supramolecular monomers to be self-assembled in a microfluidic channel.

20 Claims, 7 Drawing Sheets

(51) Int. Cl.
G01N 21/76 (2006.01)
D01F 6/94 (2006.01)

(56) References Cited

U.S. PATENT DOCUMENTS

| | | | | |
|---|---|---|---|---|
| 2010/0129634 A1* | 5/2010 | Lopez et al. | | 428/221 |
| 2010/0200494 A1* | 8/2010 | Storer et al. | | 210/510.1 |
| 2010/0279955 A1 | 11/2010 | Miyachi et al. | | |
| 2011/0008406 A1* | 1/2011 | Altman et al. | | 424/423 |
| 2011/0101276 A1* | 5/2011 | Rybtchinski | | C07D 471/06 252/301.16 |

OTHER PUBLICATIONS

Biodegradable Metters, Hydrogels: Tailoring Properties and Function through Chemistry and Structure, 2007, Taylor & Francis, pp. 5:22-5:23.*
Van Blitterswijk, Tissue Engineering, 2007, London Academic, pp. 464-465.*
De Greef, Supramolecular Polymers, May 2008, Materials Science, vol. 453, Issue 8, pp. 171-173.*
Zilberman, Novel composite Fiber structures to provide drug/protein delivery for medical implants and tissue regeneration, 2007, Acta Biomaterialia, 3 51-57.*
Lopez, U.S. Appl. No. 12/623,330, Figure 1.*
Lee, K., Synthesis of Cell-Laden Alginate Hollow Fibers Using Microfluidic Chips and Microvascularized Tissue-Engineering Applications, Small, 2009, 5, No. 11, 1264-1268.*
Alginate, accessed Jul. 16, 2014, http://www1.lsbu.ac.uk/water/hyalg.html.*
Ciferri, Supramolecular Polymers, Taylor and Francis, 2005, Second edition, p. 42.*
Lewin, Handbook of Fiber Chemistry, Taylor and Francies, 2006, Third Edition, Section 6.4 & 6.5.*
Mithun, Silk and its degumming Process, retrieved Aug. 12, 2015, http://www.textiletoday.com.bd/oldsite/magazine/574.*
Rehm, Bionanotechnology, Caister Academic Press, 2013, p. 149.*
Imae, Structures of Fibrous Supramolecular Assemblies Constructed by Amino Acid Surfactants: Investigation by AFM, SANS, and SAXS, Journal of Colloid and Interface Science 225, 285-290 (2000).*
Wonje Jeong et al., "Hydrodynamic microfabrication via "on the fly" photopolymerization of microscale fibers and tubes", Lab Chip, vol. 4, 2004, pp. 576-580.
Daisuke Kiriya et al., "MEMS Meets Supramolecules; Aligning Supramolecular Fibers Within Hydrogel Strand Using a Microfluidic Channel", The 23rd IEEE International Conference on Micro Electro Mechanical Systems (MEMS2010), Jan. 20, 2010.
Search report from International Application No. PCT/JP2010/066131, mail date is Oct. 26, 2010.
English Translation of International Preliminary Report on Patentability and Written Opinion issued with respect to counterpart International Application No. PCT/JP2010/066131, dated Sep. 13, 2012.
International Preliminary Report on Patentability and Written Opinion issued with respect to counterpart International Application No. PCT/JP2010/066131, dated Jun. 7, 2011.
Ikeda et al. "Mechanical Reinforcement of a Supramolecular Hydrogel Comprising an Artificial Glyco-Lipid through Supramolecular Copolymerization," Macromolecular Bioscience, 2008, vol. 8, No. 11, p. 1019-1025.
Abstract of Annual Congress of the Chemical Society of Japan, 2007, vol. 87, No. 2, p. 1341 (1 K2-15).
Japanese Office Action in counterpart application No. 2011-550788 dated Jun. 19, 2014 (with partial English-language translation).

* cited by examiner

PROCESS FOR PRODUCING SUPRAMOLECULAR FIBER

TECHNICAL FIELD

The present invention relates to a method for preparing a linearly extended supramolecular fiber.

BACKGROUND ART

Figure 1:
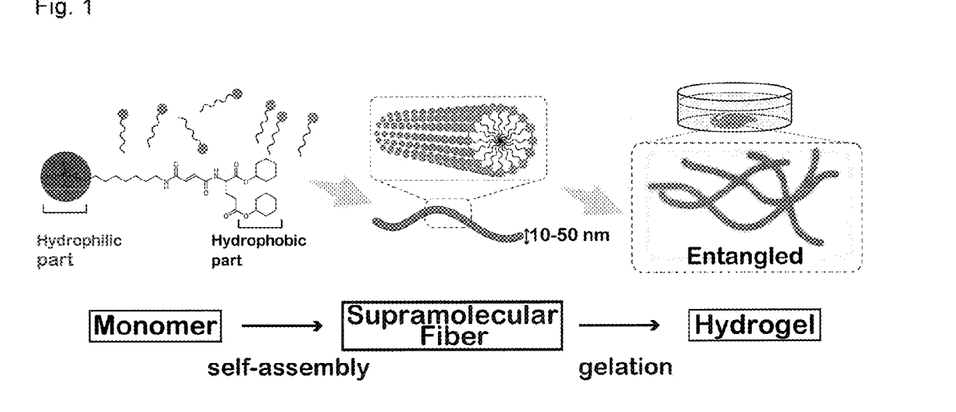
FIG. 1 This figure shows a schematic diagram of the process in which a supramolecular fiber is formed by self-assembly of supramolecular monomers, and supramolecular hydrogel is further formed.

Supramolecular hydrogel is a non-covalent hydrogel comprising self-assembled supramolecular hydrogelator molecules, which is specifically explained in, for example, Dojin News, 118, pp. 1-17, 2006. The molecules constituting supramolecular gel (these molecules may be referred to as "supramolecular monomers" for convenience) generally have a hydrophobic moiety as well as a hydrophilic moiety, and these supramolecular monomers self-assemble to form thermodynamically stable micellar fibers. Supramolecular hydrogel is formed by entanglement of these three-dimensionally formed fibers (the micellar fiber shown at the center of FIG. 1 is called "supramolecular fiber" in the specification).

There has been suggested a possibility that a supramolecular hydrogel may exhibit superior function as a smart biomaterial that functions in response to an external stimulus (Nat. Biotechnol., 21, pp. 1171, 2003), and the hydrogel has recently been focused, because it is theoretically possible to control structure and function of supramolecular hydrogel by designing the monomer molecule (Dojin News, 118, pp. 1-17, 2006). Usefulness of supramolecular fibers constituting supramolecular hydrogel as a biomaterial is also expected. For example, since the supramolecular monomers bind together through non-covalent weak interaction, another substance can be incorporated into the fiber structure, and it also possible to move such a substance along the gel axis direction. Therefore, usefulness of supramolecular fibers as a molecular sensor or a molecular transporter is expected.

In order to utilize supramolecular fibers as a biomaterial, it is essential to develop a technique for linearly extend supramolecular fibers in a desired direction, and a method for aligning a plurality of supramolecular fibers. However, when supramolecular fibers are formed by self-assembly of supramolecular monomers, spontaneous three-dimensional entanglement generally occurs and thereby hydrogel is formed, and therefore it is difficult to isolate a linearly extended supramolecular fiber.

Moreover, since supramolecular fibers consist of micellar structures formed by self-assembly of supramolecular monomers, they have a problem that they are extremely fragile against physical stimuli, and it is extremely difficult to isolate supramolecular fibers, or adjust the direction of the fibers by applying external force. From these reasons, no techniques for aligning a plurality of supramolecular fibers in a given direction have so far been developed.

PRIOR ART REFERENCE

Non-Patent Document

Non-patent document 1: Dojin News, 118, pp. 1-17, 2006

SUMMARY OF THE INVENTION

Object to be Achieved by the Invention

An object of the present invention is to provide a means for preparing a linearly extended supramolecular fiber.

Another object of the present invention is to provide a method for preparing a plurality of supramolecular fibers linearly aligned in a certain direction, more specifically, a method for aligning a plurality of supramolecular fibers in a certain direction and simultaneously extending the fibers.

Means for Achieving the Object

The inventors of the present invention conducted various researches to achieve the aforementioned objects, and as a result, found that when supramolecular monomers were self-assembled in a microfluidic channel, a linear supramolecular fiber oriented in a fluid in the direction of flow of the fluid was successfully prepared, and by appropriately controlling concentration of the supramolecular monomers and/or flow rate in the microfluidic channel, a plurality of supramolecular fibers were extended in a state of being linearly aligned. They also found that a core-shell type fiber comprising a linear supramolecular fiber extended in a microfluidic channel and covered with hydrogel such as alginate gel was easily and successfully prepared. The present invention was accomplished on the basis of these findings.

The present invention thus provides a method for preparing a linear supramolecular fiber, which comprises the step of allowing supramolecular monomers to be self-assembled in a microfluidic channel.

The present invention also provides a method for preparing a bundle of fibers comprising a plurality of linearly aligned supramolecular fibers, which comprises the step of allowing supramolecular monomers to be self-assembled in a microfluidic channel.

As another aspect of the present invention, there is provided a method for preparing a gel fiber comprising a linear supramolecular fiber covered with hydrogel, which comprises the step of covering a linear supramolecular fiber, which is obtainable by allowing supramolecular monomers to be self-assembled in a microfluidic channel, with hydrogel in the microfluidic channel.

The present invention also provides a method for preparing a gel fiber comprising a bundle of fibers comprising a plurality of linearly aligned supramolecular fibers covered with hydrogel, which comprises the step of covering a bundle of fibers comprising a plurality of linearly aligned supramolecular fibers, which are obtainable by allowing supramolecular monomers to be self-assembled in a microfluidic channel, with hydrogel in the microfluidic channel.

The present invention further provides a method for preparing a linear organic polymer, which comprises the following steps: (a) the step of preparing a linear supramolecular fiber or a bundle of fibers comprising a plurality of linearly aligned supramolecular fibers by allowing supramolecular monomers to be self-assembled in a microfluidic channel; (b) the step of polymerizing monomers in the supramolecular fiber(s) to prepare a core-shell type supramolecular fiber or a bundle of core-shell type supramolecular fibers having an organic polymer in the core(s); and (c) the step of removing the supramolecular fiber(s) as the shell(s). According to a preferred embodiment, there is provided the aforementioned method, wherein the aforementioned step (a) further comprises the step of covering the supramolecular fiber(s) with alginate gel.

As still other aspects of the present invention, there are provided a linear supramolecular fiber, a gel fiber comprising a linear supramolecular fiber covered with hydrogel, a bundle of fibers comprising a plurality of linearly aligned supramolecular fibers, and a gel fiber comprising the bundle of fibers covered with hydrogel.

Effect of the Invention

According to the method of the present invention, it becomes possible to linearly extend a supramolecular fiber, which is extremely fragile against physical stimuli, and extend a plurality of supramolecular fibers as a bundle of fibers with linearly aligning the fibers. The gel fiber prepared by the method of the present invention has a core-shell structure comprising a supramolecular fiber or a bundle of supramolecular fibers covered with hydrogel, and is characterized by superior mechanical strength. By isolating this gel fiber, or molding the gel fiber into a two-dimensional or three-dimensional structure by applying an external force, and then removing the hydrogel of the shell, an arbitrary structure consisting of the supramolecular fiber or the bundle of supramolecular fibers can be prepared.

BRIEF DESCRIPTION OF THE DRAWINGS

FIG. 3(a) shows a fluorescence intensity profile showing the core-shell structure, and the top end (Top view) shown in FIG. 3(b) indicates the coaxial core-shell structure.

MODES FOR CARRYING OUT THE INVENTION

In the specification, the "supramolecular fiber" means a structure of thermodynamically stable micellar fiber formed by self-assembly of supramolecular monomers (refer to FIG. 1), and is usually a linear fiber having an external diameter of about 10 to 50 nm. In general, such supramolecular fibers are entangled to form gel in the generation process of supramolecular hydrogel. However, it should be noted that such supramolecular hydrogel is not encompassed within the term "supramolecular fiber" used in the specification.

The term "supramolecular monomer" used in the present specification means a low molecular weight compound that can form supramolecular hydrogel and a supramolecular fiber, which is an expedient term used with an assumption that the supramolecular hydrogel corresponds to a polymer. It is not meant that polymerization is required in the process of formation of the supramolecular hydrogel. The supramolecular monomer may also be referred to as "supramolecular hydrogelator".

In the present invention, the type of the supramolecular monomer is not particularly limited, and any supramolecular monomers may be used so long as they can self-assemble to form a thermodynamically stable micellar fiber. The supramolecular monomer that can form a supramolecular hydrogel typically has a hydrophobic moiety as well as a hydrophilic portion, and a linker moiety that binds the foregoing moieties, if needed. These amphipathic supramolecular monomer can be preferably used.

As a partial structure of the supramolecular monomer, for example, the monomer may have any of various functional groups such as an alkyl group, an alkenyl group, an alkynyl group, an alkoxyl group, carboxyl group, an alkoxycarbonyl group, amino group, sulfonic acid group, phosphoric acid group, hydroxyl group, and oxo group, and arbitrary combinations thereof as well as residues of arbitrary compounds such as lipid compounds, sugar compounds, peptide compounds, amino compounds, quaternary salt compounds, phosphoric acid compounds and esters thereof, carboxylic acid compounds and esters thereof, sulfonic acid compounds and esters thereof, and arbitrary combinations thereof. However, the partial structure is not limited to these examples.

The supramolecular monomer is specifically explained in, for example, Dojin News, 118, pp. 1-17, 2006, and those skilled in the art can choose an appropriate supramolecular monomer depending on an object by referring to the aforementioned publication, the publications cited therein, and the like.

A single kind of supramolecular monomer can be usually used. Two or more kinds of supramolecular monomers may be used in combination. Further, when a supramolecular fiber is formed by using a mixture of a supramolecular monomer and one or more kinds of arbitrary compounds, supramolecular fibers extend while incorporating the compound(s) into the fibers, and a bundle of fibers comprising such supramolecular fibers aligned can be obtained.

The type of the compound to be incorporated into the supramolecular fiber is not particularly limited, and the compound is retained by a hydrophilic moiety or a hydrophobic moiety of the micellar structure of the supramolecular fiber depending on the property of the compound. For example, where an amphipathic compound is used, the compound constitutes a part of the micellar structure, and oriented with the supramolecular monomer. As such a compound, a low molecular weight compound can generally be used, and for example, pharmaceutical compounds, physiologically active compounds such as neuromessengers, lipid compounds, peptide compounds, dyes, and the like can be used. However, the compounds are not limited to these examples. In order to impart a function, such as an ability to recognize another molecule, to the supramolecular fiber, one of molecules constituting a combination of molecules that specifically interact with each other may also be incorporated into the supramolecular fiber. As for such a combination of molecules, for example, the specific binding of biotin and avidin can be used. For example, when a biotinylated lipid is incorporated into a supramolecular fiber, the resulting fiber comes to have an ability to specifically recognize avidin. The term "micellar structure" used in the specification means a state of the supramolecular monomers that aggregate at the hydrophobic moieties thereof so that the hydrophilic moieties thereof are exposed outside, of which typical micellar structure is shown in FIG. 1. However, this term should not be construed in any imitative way, and the term should be construed in the broadest sense thereof.

The method of the present invention is that for preparing a linear supramolecular fiber, and is characterized to comprise the step of allowing supramolecular monomers to be self-assembled in a microfluidic channel. The term "linear" used in the specification means that the supramolecular fiber almost linearly extends. However, the term dose not mean that the fiber is in a complete linear state, and the term should be understood to mean that the supramolecular fiber is in a one-dimensionally extending state. For example, the supramolecular fiber may be curved as a whole or partially curved, or may contain a partial deformation, torsion, or the like.

An external diameter of the supramolecular fiber is generally about 10 to 50 nm, although the diameter is not particularly limited. The section of the supramolecular fiber is generally a circular shape. The section may sometimes be a shape other than a circle depending on the type of the supramolecular monomer used, or the like. The length of the supramolecular fiber is also not particularly limited. The length may be several micrometers or longer, preferably several millimeters or longer. The fiber may sometimes have a length of about several centimeters.

The method of the present invention is that for preparing a bundle of fibers comprising a plurality of linearly aligned supramolecular fibers, which comprises the step of allowing supramolecular monomers to be self-assembled in a microfluidic channel. The term "aligned" used in the specification means that a plurality of the supramolecular fibers maintain substantially parallel relations as a whole. This term should be construed in its broadest sense including the case where parallel relations are partially lost in a plurality of supramolecular fibers, the case where a part or the whole of a plurality of supramolecular fibers are twisted and overlap with one another, and the like, and the term should not be construed in any limitative way.

The term "bundle of fibers" used in the specification means an assembly comprising a plurality of aligned supramolecular fibers. The number of the supramolecular fibers contained in the bundle of fibers is not particularly limited so long as the number is 2 or larger. Generally, the number is 5 or larger, preferably 10 or larger, more preferably 20 or larger. The maximum number is also not particularly limited, which may preferably be 1,000 or smaller, more preferably 100 or smaller, still more preferably 50 or smaller.

The length of the bundle of fibers is not particularly limited. The length may be several centimeters or longer, preferably several tens of centimeters or longer. The fiber may have a length of about several meters. The external diameter of the supramolecular fiber contained in the bundle of fibers is also not particularly limited, which is generally about 10 to 50 nm. A plurality of the supramolecular fibers generally have substantially the same external diameters, or they may have different external diameters. As cross-sectional shape of the bundle of fibers, for example, the shape may be a variety of shapes including a circular shape, an elliptic shape and a polygonal shape such as a quadrilateral shape and a pentagonal shape, and the like. The shape is preferably a circular shape. The external diameter of the bundle of fibers is also not particularly limited, and can be appropriately chosen depending on the number of the fibers. For example, the diameter may be about 20 nm to 100 μm, and the external diameter can be appropriately chosen depending on a purpose of use thereof.

The microfluidic channel used in the method of the present invention is not particularly limited. It is preferable to use, for example, an apparatus having an injection hole diameter of about 130 μm that is capable of injecting a solution of supramolecular monomer into a microfluidic channel at a rate of 1 to 20 μl/minute. The internal diameter of the microfluidic channel is, for example, about 600 μm, however, the diameter is not limited to the exemplified diameter. As the microfluidic channel, for example, one described in Lab. Chip, 4, pp. 576-580, 2004 can be used.

When a solution of a supramolecular monomer is injected into a microfluidic channel, monomers move with flow of fluid in the microfluidic channel and self-assemble to form a supramolecular fiber. Depending on conditions such as monomer concentration in the solution to be injected and/or flow rate in the microfluidic channel, preferably flow rate in the microfluidic channel, a single supramolecular fiber or a plurality of supramolecular fibers are formed. The formed supramolecular fiber is oriented and extended along the direction of the flow in the microfluidic channel to give a linear supramolecular fiber. When a plurality of supramolecular fibers are formed in the microfluidic channel, a plurality of supramolecular fibers are oriented and linearly extended along the direction of the flow of the fluid, while they are aligned with one another along the direction of the flow to form a bundle of fibers comprising a plurality of supramolecular fibers.

The concentration of the supramolecular monomer to be injected into the microfluidic channel can be appropriately chosen depending on the type of the supramolecular monomer to be used, the flow rate in the microfluidic channel, the number of the supramolecular fiber to be formed in the microfluidic channel, and the like, and the concentration is not particularly limited. For example, by referring to the conditions specifically mentioned in the examples of the specification, and the like, the concentration can be easily chosen. When the concentration of the supramolecular monomer is low, in order to promote the self-assembly, metal ions or the like can also be added to the microfluidic channel. For example, by adding calcium ions or the like to the microfluidic channel, self-assembly of the supramolecular monomer may be promoted, and such an embodiment is a preferred embodiment of the present invention.

Figure 2:
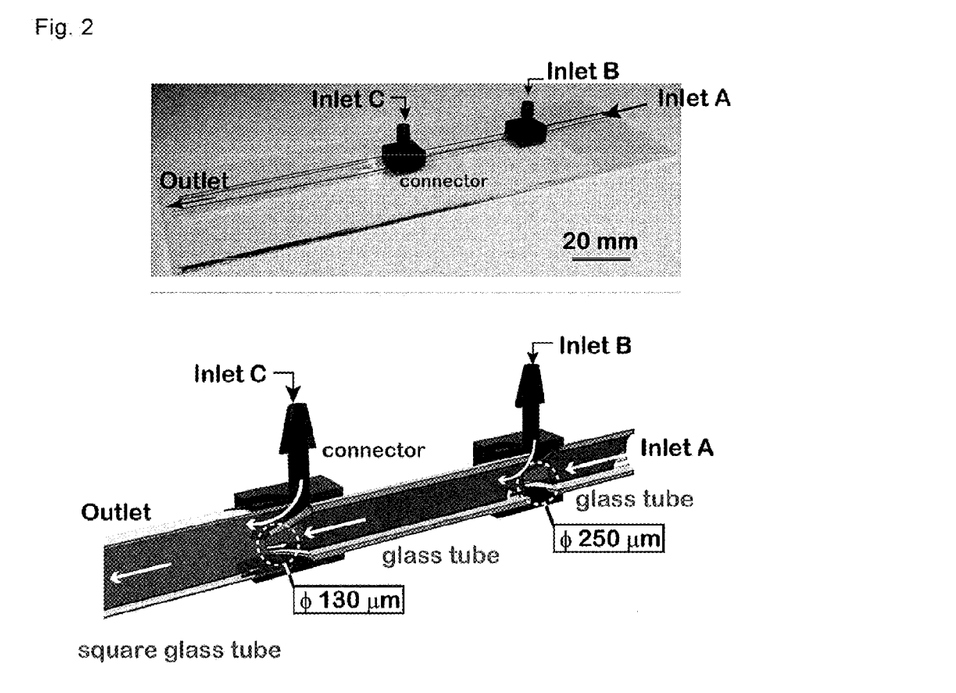
FIG. 2 This figure shows an example of double coaxial microfluidic device usable in the method of the present invention.

According to the method of the present invention, a gel fiber comprising a single supramolecular fiber or a bundle of fibers comprising a plurality of supramolecular fibers covered with hydrogel can be prepared. For such preparation, it is preferable to use a coaxial microfluidic device that can form a coaxial double-layered fluid. By using this device, two kinds of fluids can be separately and coaxially injected as a core and a shell. By injecting a supramolecular monomer solution as an internal fluid (core) and a solution of gelator that can form hydrogel as an external fluid (shell), a supramolecular fiber covered with hydrogel or a bundle of fibers covered with hydrogel can be prepared. The double microfluidic device is specifically explained in, for example, Lab Chip, 4, pp. 576-580, 2004, FIG. 1. Further, a coaxial microfluidic device preferably used in the method of the present invention is shown in FIG. 2.

As the hydrogel, there can be used, for example, hydrogel comprising chitosan gel, collagen gel, gelatin, peptide gel, fibrin gel or a mixture of these as a base material can be used. As commercially available products, for example, Matrigel (Nippon Becton Dickinson Co., Ltd.), and the like may be used. Further, hydrogel that can be formed by irradiating a water-soluble polymer such as polyvinyl alcohol, polyethylene oxide or polyvinylpyrrolidone with ultraviolet rays or radiation may also be used.

It is also preferable to use high strength hydrogel having a superior mechanical strength as the hydrogel. Although the type of the high strength hydrogel is not particularly limited, it is preferable to use hydrogel having a mechanical strength substantially the same as or higher than that of, for example, collagen gel or polyvinyl alcohol hydrogel. Examples of such gel include, for example, alginate gel and agarose gel; however, the gels are not limited to these examples. Further, as the high strength hydrogel, hydrogel can be preferably used which has a property of being gelled in the presence of metal ions such as calcium ions. From such a point of view, alginate gel is preferred. Further, agarose gel or photocurable gel that is cured by UV irradiation or the like can also be used. As for the mechanical strength of the gel, tensile strength, load strength, and the like can be measured by a method of using a tensile tester in water or the like according to the methods well known to those skilled in the art.

The gel fiber comprising a single supramolecular fiber or a bundle of fibers comprising a plurality of supramolecular fibers covered with hydrogel may be covered with a single kind of hydrogel. The fiber may be covered with, for example, multiple layers consisting of two or more kinds of different kinds of hydrogels. For example, the fiber may have two or more kinds of hydrogels having different strengths, for example, a cover consisting of polyvinyl alcohol hydrogel and a cover consisting of alginate gel formed outside. The external diameter of the gel fiber having a core-shell structure is not particularly limited, which may be, for example, in the range of 200 nm to 2,000 µm, preferably in the range of 50 to 1,000 µm.

Preparation of the supramolecular fiber, the bundle of fibers, and the gel fiber can generally be conducted by using water as a solvent. A hydrophilic organic solvent having a water-miscible property, for example, ethanol, acetone, ethylene glycol, propylene glycol, glycerol, dimethylformamide, dimethyl sulfoxide, and the like may be added to the water. In order to increase the strength of the supramolecular fiber or the hydrogel, an appropriate ingredient or a solvent can also be blended. From such a point of view, for example, it is also possible to add dimethyl sulfoxide as a solvent for the preparation of polyvinyl alcohol hydrogel.

In order to prepare a linear gel fiber comprising a supramolecular fiber or a bundle of fibers covered with hydrogel such as alginate gel by using the double coaxial microfluidic device shown in FIG. 2, for example, a supramolecular monomer solution for preparing a supramolecular fiber constituting the core can be charged from the inlet A and injected from an injection hole, a sodium alginate solution before crosslinking can be charged from the inlet B and coaxially injected from the injection hole to form a fluid comprising coaxial core and shell, an aqueous solution containing $CaCl_2$ is introduced into the fluid from the inlet C to cause gelation of the alginate of the shell, and at the same time the supramolecular monomers of the core can be allowed to be self-assembled to form a supramolecular fiber or a bundle of fibers, and thereby a gel fiber is constructed which comprises a supramolecular fiber or a bundle of fibers in the inside (core) and alginate gel in the outside layer (shell as a cover). By appropriately adjusting the injection rates of the core and/or the shell, the diameter of the core and the covering thickness of the shell can be appropriately adjusted. The introduction rate of the aqueous solution containing calcium ions is also not particularly limited, which may be, for example, about 1 to 10 ml/minute.

When the bundle of supramolecular fibers prepared by the method of the present invention has a sufficient external diameter, or when such bundle of supramolecular fiber is covered to form a gel fiber, one or more kinds of biogenic substances such as cells, proteins, lipids, saccharides, nucleic acids, and antibodies may be added into the moiety of the bundle of fibers and/or hydrogel. The type of the cells is not particularly limited, and examples include, for example, ES cells and iPS cells having pluripotency, various kinds of stem cells having multipotency (hematopoietic stem cells, neural stem cells, mesenchymal stem cells and the like), stem cells having unipotency (liver stem cells, reproduction stem cells and the like), as well as various kinds of differentiated cells, for example, myocytes such as skeletal muscle cells and cardiac muscle cells, nerve cells, fibroblasts, epithelium cells, hepatocytes, beta cells of pancreas, skin cells, and the like. However, the cells and biogenic substances are not limited to those exemplified above. Further, to the aforementioned bundle of fibers or gel fiber, for example, fibers such as carbon nanofibers, inorganic substances such as catalytic substances, beads covered with antibodies, or artifacts such as microchips may be added.

As explained above, an ability to recognize various molecules or biopolymers can be imparted to the supramolecular fiber. For example, by imparting an ability to recognize metal, metal particles (those of Au, Pt, Pd or the like) can be one-dimensionally arranged on the surface of the supramolecular fiber. By aggregating the metal particles on the surface of the supramolecular fiber obtained as described above to a high concentration, a supramolecular fiber covered with a metal can also be prepared, and a gel fiber having the supramolecular fiber covered with a metal as a core can also be prepared. Further, as explained above, it is possible to incorporate various molecules into the inside of the supramolecular fiber. For example, monomers of an organic polymer (for example, thiophene and the like) can be incorporated into the inside of the supramolecular fiber to prepare a highly oriented fibrous organic polymer by using the supramolecular fiber as a template, and further, a gel fiber having a supramolecular fiber comprising a bundle of fibrous organic polymers as a core can also be prepared. The type of the monomer of the organic polymer is not particularly limited. For example, various kinds of monomers including conductive pi-conjugated molecules can be used.

Further, by removing the supramolecular monomers forming the shell part from the core-shell type supramolecular fiber having the fibrous organic polymer as the core obtained as described above, the organic polymer formed in the shape of a fiber can also be isolated. The supramolecular fiber can be easily removed by destroying the self-assembled state of the supramolecular monomers by adding an appropriate physicochemical stimulus, such as change of pH and change of temperature. The embodiment in which the supramolecular fiber or the bundle of supramolecular fibers is used as a template for forming a fibrous organic polymer is also a preferred embodiment of the present invention. When the supramolecular fiber or the bundle of supramolecular fibers is used as a template, it is also preferable to cover the outside of the supramolecular fiber or the bundle of supramolecular fibers with high strength gel, such as alginate gel, in order to improve the strength. In this case, for example, by removing the alginate gel, and then removing the supramolecular fiber, a fibrous organic polymer can be isolated.

By removing the hydrogel of the shell from the gel fiber of a core-shell structure obtained by the method of the present invention, if necessary, a supramolecular fiber or a bundle of supramolecular fibers can be exposed. For example, by preparing a gel fiber having a core-shell structure comprising a supramolecular fiber or a bundle of fibers covered by using alginate gel as the hydrogel, and then allowing a chelating agent, such as EDTA, to react on the fiber at an appropriate concentration to remove the calcium ions and thereby remove only the hydrogel, the supramolecular fiber or a bundle of the supramolecular fibers can be prepared. The aforementioned operation for the removal may be performed after the gel fiber is appropriately molded.

By this method, an arbitrary two-dimensional or three-dimensional structure can be prepared with the supramolecular fiber or the bundle of supramolecular fibers. For example, by preparing a gel fiber of a core-shell structure, constructing a three-dimensional structure of a specific structure with the fiber, and then removing the shell, a structure of the supramolecular hydrogel having a desired microstructure can be prepared. Further, by preparing a woven fabric structure with the gel fiber having a core-shell structure, and then removing the shell, a supramolecular hydrogel of the woven fabric structure can also be prepared. By using alginate gel fibers, agarose gel fibers, or the like for the preparation of a three-dimensional structure or a woven fabric structure, a three-dimensional structure or a woven fabric structure comprising a composite material can also be prepared. A purpose of use of the linear supramolecular fiber or the bundle of supramolecular fibers, the gel fiber having a core-shell structure prepared by the method of the present invention, and the aforementioned two-dimensional or three-dimensional structure is not particularly limited. The fibers can be used as biomaterials for various uses, such as various kinds of sensors, transporters of various substances, and cell culture.

Further, if necessary, by removing the supramolecular fiber or the bundle of supramolecular fibers of the core from the gel fiber having a core-shell structure, a hollow fiber consisting of the hydrogel can also be prepared. For example, by preparing a gel fiber by covering a supramolecular fiber or a bundle of supramolecular fibers with agarose gel as the hydrogel, and then destroying the self-assembled state of the supramolecular monomers by adding an appropriate physicochemical stimulus, such as change of pH and change of temperature, the core can be removed. The aforementioned operation for the removal may be performed after the gel fiber is appropriately molded.

EXAMPLES

The present invention will be more specifically explained with reference to examples. However, the scope of the present invention is not limited to the following examples.

Example 1

A gel fiber having a core-shell structure and a diameter of 80 μm was prepared by using a double coaxial laminar flow device shown in FIG. 2 (Lab. Chip, 4, pp. 576, 2004, FIG. 1). As a fluid for the core, a 0.1% w/v aqueous solution of a phosphate head type supramolecular monomer (the compound having the structure shown on the left side of FIG. 1, J. Am. Chem. Soc., 131, pp. 5580-5585, 2009) was used, and as a fluid for the shell, a 1.5% w/v sodium alginate aqueous solution was used. As a fluid for the sheath, a 20 mM calcium chloride solution ($Q_{sheath}$=3.2 ml/min) was used.

Figure 3:
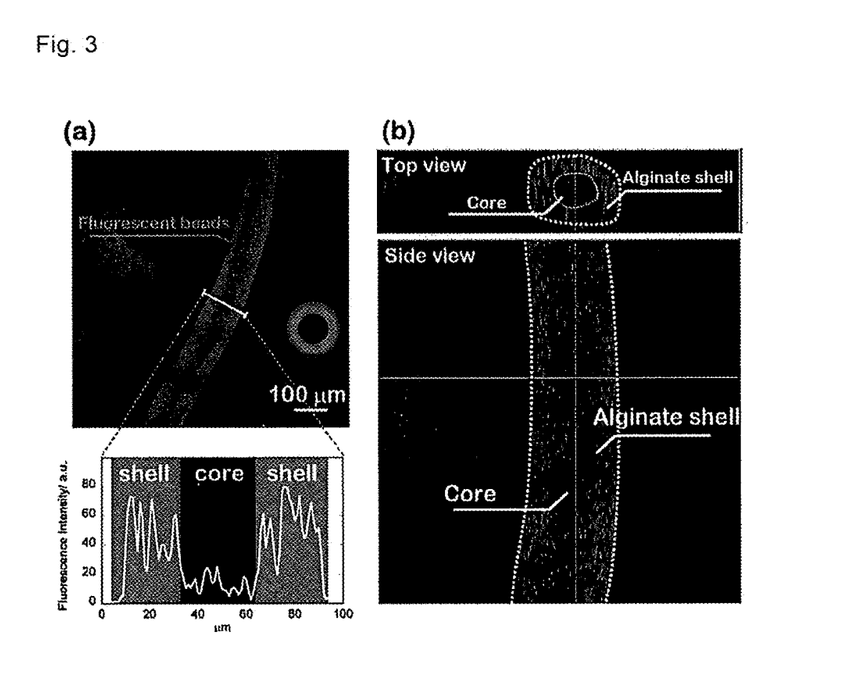
FIG. 3 This figure shows a gel fiber of a core-shell structure obtained by the method of Example 1.
Figure 4:
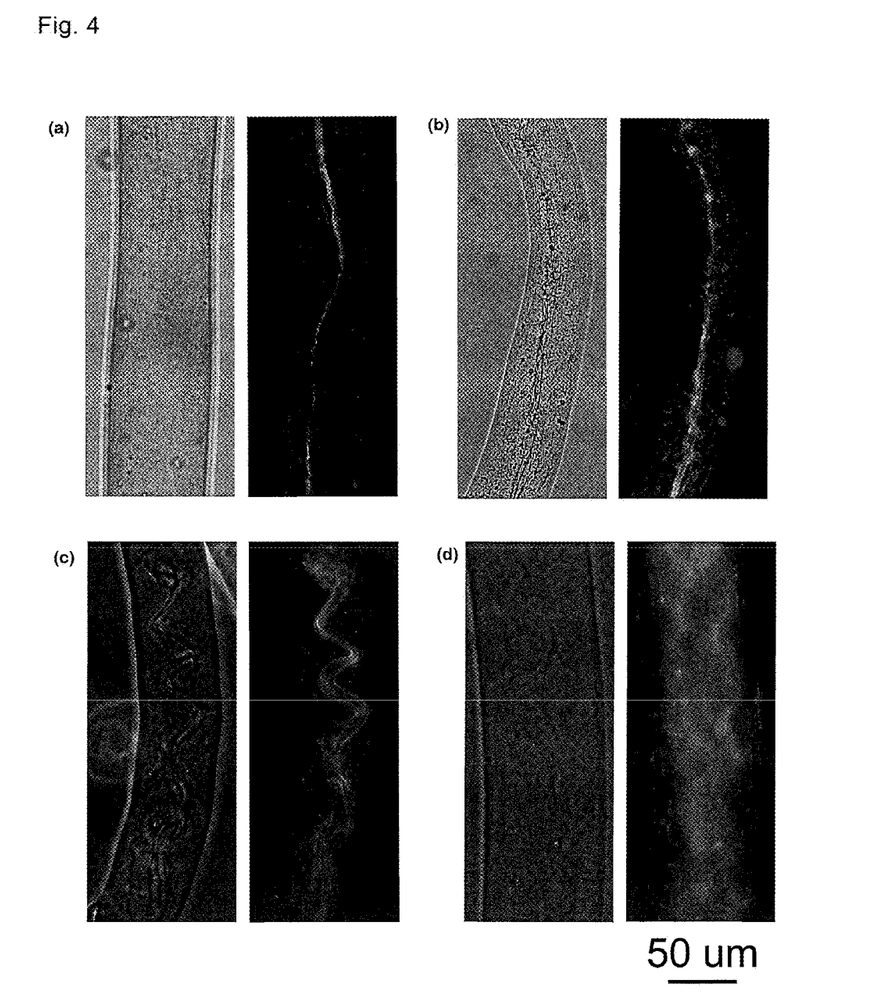
FIG. 4 This figure shows that the core diameter and covering thickness of the shell in the gel fiber are varied depending on the flow rate ratio of the core fluid and the shell fluid ($Q_{core}/Q_{shell}$). In the figure, results of (a) core (supramolecular fiber): 1 μl/min, shell (sodium alginate gel): 19 μl/min; (b) core (supramolecular fiber): 5 μl/min, shell (sodium alginate gel): 15 μl/min; (c) core (supramolecular fiber): 10 μl/min, shell (sodium alginate gel): 10 μl/min; and (d) core (supramolecular fiber): 15 μl/min, shell (sodium alginate gel): 5 μl/min are shown, in which each of fluorescence image and bright field image is shown.

The fiber was prepared by adding fluorescent beads (carboxylic acid-modified microspheres, red, ϕ 200 nm) to the 1.5% w/v sodium alginate aqueous solution as the fluid for shell. The resulting gel fiber having a core-shell structure is shown in FIG. 3. Presence of the fluorescent beads incorporated into the alginate gel was confirmed on the basis of the fluorescence intensity profile shown in FIG. 3, (a), and it was proved that the resulting gel fiber has a coaxial core-shell structure. The coaxial core-shell structure was successfully confirmed also from the cross-sectional image of the gel fiber (top end shown in FIG. 3, (b), Top view). This gel fiber had a mechanical strength such that the fiber was handled with a pair of tweezers. The core diameter and the covering thickness of the shell in the resulting gel fiber changed depending on the flow rate ratio of the core fluid and the shell fluid ($Q_{core}/Q_{shell}$) (FIG. 4).

Figure 5:
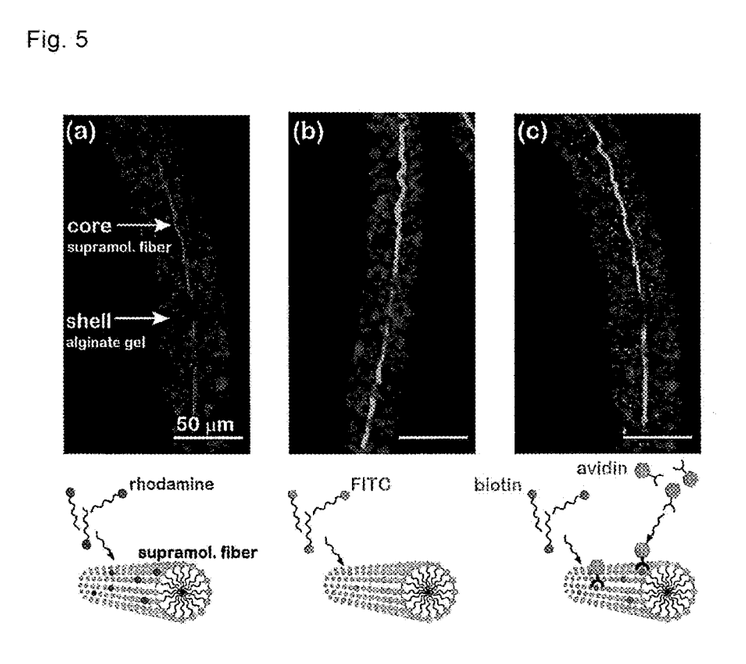
FIG. 5 This figure shows the cores of the gel fibers of a core-shell structure imaged with fluorescence using fluorescent lipid incorporated into the cores. Each view of incorporation of (a) rhodamine lipid (red), (b) FITC lipid (green), and (c) biotinylated lipid (green) into the supramolecular fibers as the cores is shown. The lower diagrams are conceptual sketches of the incorporated fluorescent lipids.

In the same manner, gel fibers were prepared by adding a mixture (1 to 1.5 mM) of amphipathic octadecyl rhodamine B chloride (red) or FITC lipid (fluorescein isothiocyanate-labeled lipid, green), and fluorescent beads (carboxylic acid-modified microspheres, blue, ϕ 1 μm) to the 1.5% w/v sodium alginate aqueous solution as the fluid for the shell. The amphipathic fluorescent lipid was selectively incorporated into the supramolecular fiber of the core, and as a result, the supramolecular structure was successfully visualized. The results are shown in FIG. 5. The blue fluorescence indicates the alginate gel of the shell incorporating the fluorescent beads, and it is clear from the results shown in FIGS. 5(a) and (b) that the rhodamine lipid (red) and the FITC lipid (green) were incorporated into the supramolecular fiber of the core.

Further, a gel fiber in which a biotinylated lipid was incorporated into the supramolecular fiber of the core was prepared. Biotin in this gel fiber was visualized with a streptavidin-bound dye (Streptavidin Alexa Fluor 488, green, Invitrogen), and the result is shown in FIG. 5, (c). It is clear from the result that the supramolecular fiber recognized the streptavidin-bound dye through the specific binding of biotin and avidin, and it is demonstrated that the supramolecular fiber and the gel fiber provided by the present invention can be applied as members of sensors, diagnostic tools, and the like.

Figure 6:
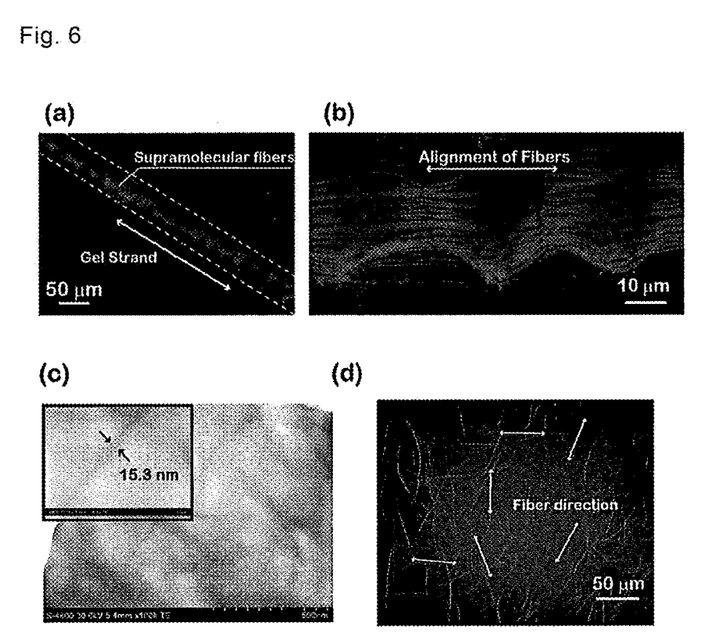
FIG. 6 This figure shows the results of confocal laser scanning microscopy of a bundle of fibers comprising a plurality of linearly aligned supramolecular fibers. The view (b) shows a magnified view of (a). The view (c) shows the result of transmission electron microscopy of supramolecular hydrogel prepared in a flask as a control, and (d) shows the result of confocal laser scanning microscopy of a supramolecular fiber of a gel fiber prepared by flowing sodium alginate (1.5 wt %) and supramolecular monomers (0.1 wt %) in a double coaxial microfluidic channel and stained with rhodamine B chloride.

A gel fiber in which a fluorescence lipid was incorporated into a supramolecular fiber was prepared in the same manner, and observed under a confocal laser scanning microscope. As a result, a bundle of fibers comprising a plurality of linearly aligned supramolecular fibers was observed. The results are shown in FIG. 6. FIG. 6(b) is a magnified view (a), and a plurality of supramolecular fibers oriented in the extension direction of the linear gel fiber can be confirmed.

As a control, a supramolecular hydrogel (supramolecular monomer: 0.1%) was prepared in a flask, and observed with a transmission electron microscope (TEM). The result is shown in FIG. 6(c). A network in which the supramolecular fibers were three-dimensionally and randomly entangled was formed, and neither isolated linear supramolecular fiber nor linearly aligned supramolecular fibers were observed. Further, hydrogel formed from sodium alginate and supramolecular monomers (15:1, wt %) and stained with rhodamine B chloride was observed with a confocal laser scanning microscope. As a result, a random three-dimensional network constituting the gel was observed (FIG. 6, (d)). These results demonstrated that neither isolated linear supramolecular fiber nor linearly aligned supramolecular fibers are generally formed in the supramolecular hydrogel, and that a bundle of fibers comprising a plurality of linearly aligned supramolecular fibers can be prepared by the method of the present invention.

Figure 7:
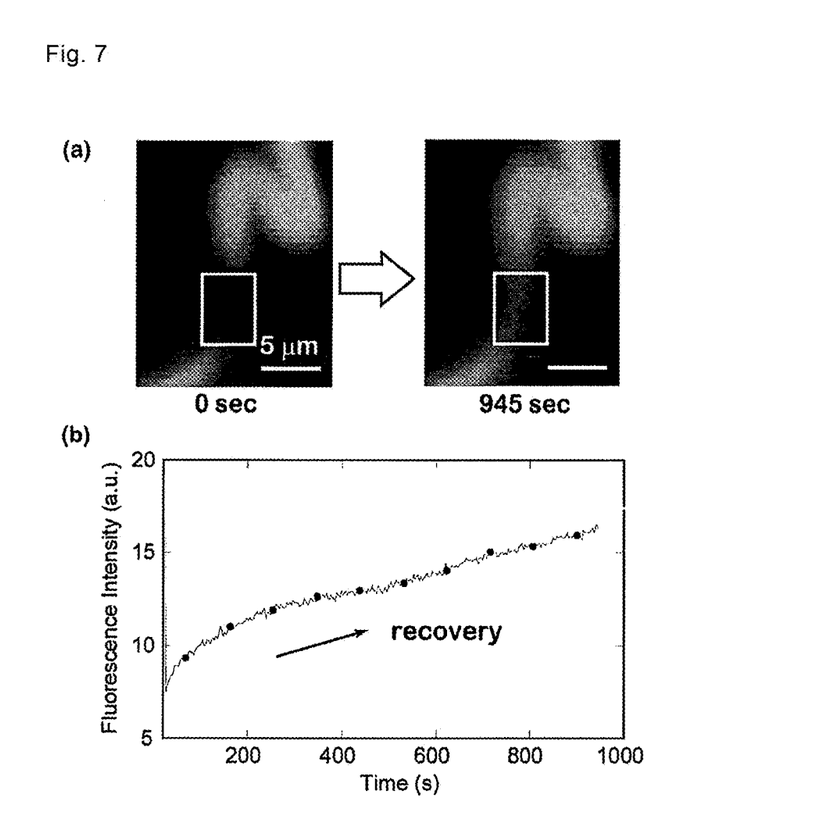
FIG. 7 This figure shows results of examination in which fluorescence of a part of the core of a core-shell type supramolecular fiber incorporating FITC lipids was photobleached with a laser of 488 nm, and recovery process of the fluorescence intensity after the photobleaching was investigated. The view (a) shows confocal laser scanning microscope images obtained immediately after the irradiation (0 sec) and aster 946 seconds, in which the rectangles indicate the laser-irradiated region, and (b) shows change of fluorescence intensity of the irradiation region over time.

In order to confirm the molecular flow characteristics in the resulting bundle of fibers comprising supramolecular fibers, a part of the core (diameter of core: 1 μm) of the core-shell type supramolecular fiber incorporated with the FITC lipid was photobleached at room temperature with a laser of 488 nm, and the recovery process of the fluorescence intensity after the photobleaching was investigated (FRAP: fluorescence recovery after photobleaching). By this method, migration degree of the fluorescence-labeled substance can be measured on the basis of the recovery characteristics of fluorescence intensity of the fluorophore of the substance. The recovery of fluorescence provided by migration of non-photobleached fluorophores to the photobleached portions was monitored over time. The results are shown in FIG. 7. FIG. 7(a) shows confocal laser scanning microscope images obtained immediately after the irradiation (0 sec) and 946 seconds thereafter. The laser was irradiated on the region enclosed with the rectangle. FIG. 7(b) shows the recovery of fluorescence over time in the irradiated region. As a result, 16% of recovery of the fluorescence intensity was confirmed after 946 seconds, and slow diffusion and fluidic nature in the supramolecular fiber were demonstrated.

Example 2

Figure 8:
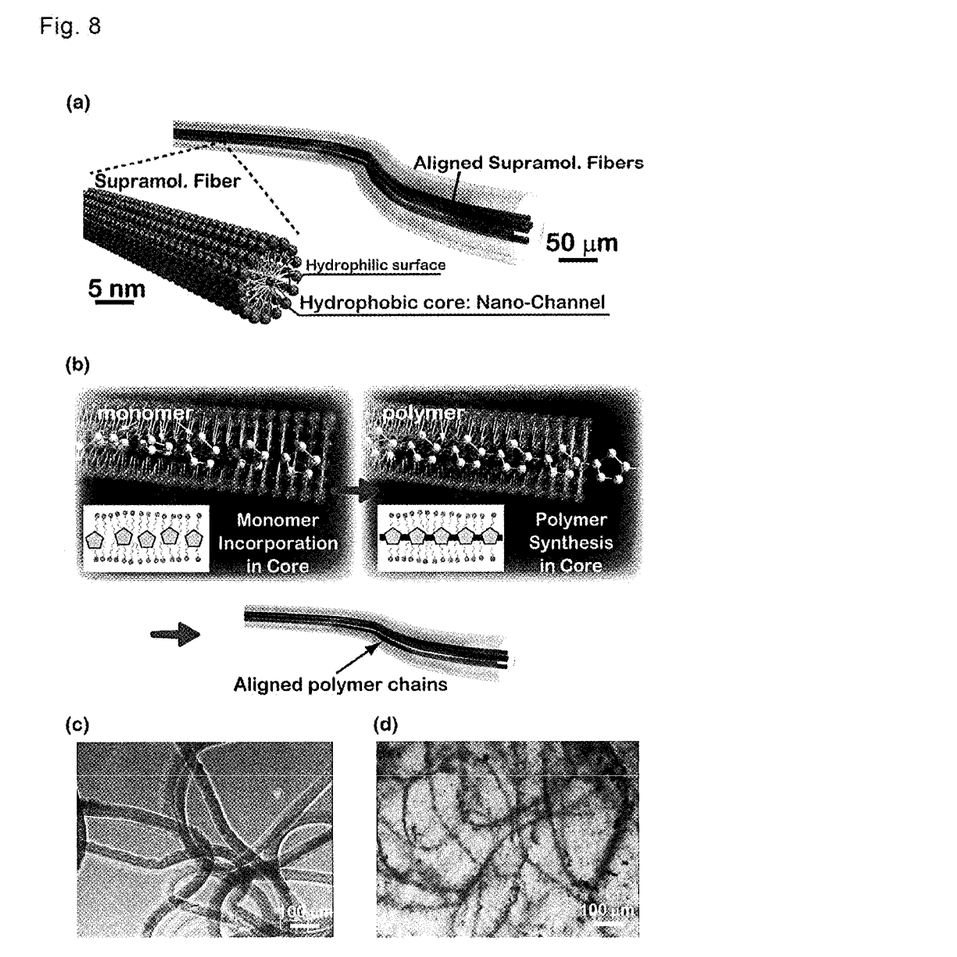
FIG. 8 This figure shows a method for preparing a fibrous organic polymer by using a supramolecular fiber as a template. Schematic diagrams of the method ((a) and (b)), (c) microphotograph of the supramolecular fiber and the fibrous organic polymer covered with alginate gel, and (d) microphotograph of the fibrous polymer obtained by removing the supramolecular fiber and the alginate gel are shown.

A fibrous organic polymer was prepared by using a hydrophobic nanospace existing in the inside of a supramolecular fiber as a template. Schematic diagrams of the preparation method are shown in FIGS. 8(a) and (b). A supramolecular fiber covered with alginate gel was prepared in the same manner as that of Example 1 with the conditions that a 0.1% w/v aqueous solution of a phosphate head type supramolecular monomer as the supramolecule was used as a fluid for the core and a 1.5% w/v sodium alginate aqueous solution was used as a fluid for the shell. A 20 mM calcium chloride solution was used as a fluid for the sheath. The diameter of the internal space of this supramolecular fiber was about 5 to 10 nm. A solution of 3,4-ethylenedioxythiophene as a monomer of organic polymer dissolved in dimethyl sulfoxide was filled in the inside of the supramolecular fibers by immersing the supramolecular fibers in the solution, and polymerization was attained by oxidation polymerization. FIG. 8(c) shows a microphotography of the polymers covered with the supramolecular fibers and alginate gel. By removing the alginate gel from the resulting fibers using a chelating agent, and further removing the supramolecular fibers with a $Ca^{2+}$ chelating agent, a bundle of polymers comprising a plurality of the formed fibrous organic polymers was obtained. The diameter of the fibrous organic polymer was about 20 to 30 nm, which substantially reflected the diameter of the supramolecular fiber, and the length of the fiber was at least in the millimeter scale. A microphotography of the fibrous organic polymers was shown in FIG. 8(d).

What is claimed is:

1. A bundle of fibers comprising;
   a plurality of linearly aligned core-shell supramolecular fibers obtained by allowing supramolecular monomers to be self-assembled in a microfluidic channel by injecting a solution of a supramolecular monomer into the microfluidic channel to allow the monomers to move with a flow of fluid in the microfluidic channel and self-assemble to form the plurality of supramolecular fibers linearly aligned with each other, wherein
   the supramolecular monomers have a hydrophilic end and a hydrophobic end, and
   the core of each core-shell supramolecular fiber comprises a hydrophobic portion of the supramolecular monomers and the shell of each core-shell supramolecular fiber comprises a hydrophilic portion of the supramolecular monomers.

2. A bundle of fibers according to claim 1, comprising 3 or more linearly aligned core-shell supramolecular fibers.

3. A bundle of fibers according to claim 1, comprising 5 or more linearly aligned core-shell supramolecular fibers.

4. A bundle of fibers according to claim 1, wherein the supramolecular monomers do not have amino groups.

5. A gel fiber comprising:
   a bundle of fibers comprising a plurality of linearly aligned core-shell supramolecular fibers covered with hydrogel, wherein
   the bundle of fibers comprising the plurality of linearly aligned core-shell supramolecular fibers is formed by injecting the solution of a supramolecular monomer into the microfluidic channel to allow the supramolecular monomers to move with a flow of fluid in the microfluidic channel and self-assemble to form the plurality of linearly aligned core-shell supramolecular fibers, and wherein
   the core of each core-shell supramolecular fiber comprises a hydrophobic portion of the supramolecular monomers and the shell of each core-shell supramolecular fiber comprises a hydrophilic portion of the supramolecular monomers.

6. The gel fiber according to claim 5, which has an external diameter in the range of 200 nm to 2,000 μm.

7. The gel fiber according to claim 5, which has an external diameter in the range of 50 to 1,000 μm.

8. The gel fiber according to claim 5, wherein the hydrogel is selected from the group consisting of chitosan gel, collagen gel, gelatin, peptide gel, fibrin gel, alginate gel, and agarose gel.

9. A gel fiber according to claim 5, wherein the supramolecular monomers do not have amino groups.

10. A bundle of fibers comprising a plurality of linearly aligned core-shell supramolecular fibers, wherein the core of each core-shell supramolecular fiber comprises a hydrophobic portion of at least one supramolecular monomer and the shell of each core-shell supramolecular fiber comprises a hydrophilic portion of the at least one supramolecular monomer, and the at least one supramolecular monomer has a hydrophobic end and a hydrophilic end.

11. A bundle of fibers according to claim 10, comprising 3 or more linearly aligned core-shell supramolecular fibers.

12. A bundle of fibers according to claim 10, comprising 5 or more linearly aligned core-shell supramolecular fibers.

13. A bundle of fibers according to claim 10, wherein the core of at least one of the core-shell supramolecular fibers also comprises an organic polymer.

14. A bundle of fibers according to claim 10, wherein the core-shell supramolecular fibers do not comprise supramolecular have amino groups.

15. A gel fiber comprising a bundle of fibers comprising a plurality of linearly aligned core-shell supramolecular fibers covered with hydrogel, wherein the core of each core-shell supramolecular fiber comprises a hydrophobic portion of at least one supramolecular monomer and the shell of each core-shell supramolecular fiber comprises a hydrophilic portion of the at least one supramolecular monomer.

16. A gel fiber according to claim 15, wherein the core of at least one of the core-shell supramolecular fibers also comprises an organic polymer.

17. A gel fiber according to claim 15, wherein the core-shell supramolecular fibers do not comprise supramolecular monomers that have amino groups.

18. A method for preparing the bundle of fibers of claim 10, which comprises:

allowing supramolecular monomers to be self-assembled in a microfluidic channel by injecting a solution of a supramolecular monomer into the microfluidic channel to allow the monomers to move with a flow of fluid in the microfluidic channel and self-assemble to form the plurality of supramolecular fibers linearly aligned with each other.

19. A method for preparing a linear organic polymer, which comprises:

(a) preparing the bundle of fibers according to claim 10 by allowing supramolecular monomers to be self-assembled in a microfluidic channel by injecting a solution of a supramolecular monomer into the microfluidic channel to allow the monomers to move with a flow of fluid in the microfluidic channel and self-assemble to form the bundle of fibers;

(b) polymerizing monomers in at least one core of the linearly aligned core-shell supramolecular fibers to form an organic polymer in the at least one core of the linearly aligned core-shell supramolecular fibers; and (c) removing the linearly aligned core-shell supramolecular fibers.

20. A method for preparing the gel fiber of claim 15, which comprises:

covering a bundle of fibers comprising a plurality of linearly aligned core-shell supramolecular fibers linearly, which is obtained by allowing supramolecular monomers to be self-assembled in a microfluidic channel by injecting a solution of a supramolecular monomer into the microfluidic channel to allow the monomers to move with a flow of fluid in the microfluidic channel and self-assemble to form the plurality of linearly aligned core-shell supramolecular fibers, with hydrogel in the microfluidic channel.

\* \* \* \* \*

UNITED STATES PATENT AND TRADEMARK OFFICE
CERTIFICATE OF CORRECTION

PATENT NO. : 9,476,834 B2
APPLICATION NO. : 13/522155
DATED : October 25, 2016
INVENTOR(S) : S. Takeuchi et al.

Page 1 of 1

It is certified that error appears in the above-identified patent and that said Letters Patent is hereby corrected as shown below:

In the Claims

Column 13, Lines 16, 17 Claim 14, Lines 2, 3 change "supramolecular have amino" to
-- supramolecular monomers that have amino --

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*